United States Patent [19]

Kötzsch et al.

[11] 4,060,538
[45] Nov. 29, 1977

[54] PROCESS FOR THE PREPARATION OF SILANE ESTERS OF TERTIARY ALCOHOLS

[75] Inventors: Hans Joachim Kötzsch, Rheinfelden; Hans-Joachim Vahlensieck, Wehr; Claus-Dieter Seiler, Rheinfelden, all of Germany

[73] Assignee: Dynamit Nobel Aktiengesellschaft, Troisdorf Berz. Cologne, Germany

[21] Appl. No.: 436,759

[22] Filed: Jan. 25, 1974

[30] Foreign Application Priority Data

Jan. 31, 1973 Germany .............................. 2304503

[51] Int. Cl.² .......................... C07F 7/04; C07F 7/18
[52] U.S. Cl. ....................... 260/448.8 R; 260/448.8 A
[58] Field of Search ................... 260/448.8 R, 448.8 R

[56] References Cited

U.S. PATENT DOCUMENTS

| 2,566,957 | 9/1951 | Pedlow et al. | 260/448.8 R |
| 2,645,624 | 7/1953 | Hunter | 260/448.8 R X |
| 2,995,590 | 8/1961 | Peeler et al. | 260/448.8 A |
| 3,261,807 | 7/1966 | Bluestein | 260/448.8 R X |

*Primary Examiner*—Paul F. Shaver
*Attorney, Agent, or Firm*—Burgess, Dinklage & Sprung

[57] ABSTRACT

An alkoxysilane of the formula

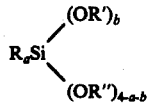

wherein:
R is hydrogen, an alkyl radical of 1 to 4 carbon atoms or an alkenyl radical of $C_2$-$C_{10}$;
R' is alkyl;
R" is tertiary alkyl;
$a$ is 1 or 2;
$b$ is 1 or 2;
$a + b$ does not exceed 3; and a process for preparing such alkoxysilane by the steps of:

a. contacting in the liquid phase and without contacting in the gas phase a halogen silane of the formula

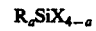

wherein R is hydrogen, alkenyl of $C_2$-$C_{10}$ or alkyl of $C_1$-$C_4$, $a$ is 1 or 2 and X is halogen with a primary or secondary alcohol having the formula R'OH wherein R' is an alkyl group, an alkylene group or a polymer hydroxyalkylene group having a terminal alkyl ether grouping, said alcohol present in an amount not in excess of a 10% stoichiometric excess whereby to produce a halogen alkoxysilane; and b. thereafter contacting said halogen alkoxysilane with an alcohol of the formula R"OH wherein R" is a tertiary alkyl group of $C_4$-$C_8$ in the presence of an acid-binding agent.

32 Claims, No Drawings

PROCESS FOR THE PREPARATION OF SILANE ESTERS OF TERTIARY ALCOHOLS

BACKGROUND OF THE INVENTION

1. Field of the Invention

This invention is directed to a process for the preparation of silane esters of tertiary alcohols obtained by a two-step process in which in a first step a halogen silane is reacted with a primary or secondary alcohol to produce a halogen alkoxy silane and the resultant halogen alkoxy silane is reacted in a second step with a tertiary alcohol whereby there is formed a silane ester of a tertiary alcohol. This invention is also directed to a method for obtaining silane esters of tertiary alcohols in pure form. This invention is particularly directed to the silane esters of tertiary alcohols per se and to an improved process whereby they are obtained in relatively pure form. The process is directed to compounds such as tertiary butoxyalkoxysilanes.

DISCUSSION OF THE PRIOR ART

The reaction of hydrogen silanes with primary, secondary and tertiary alcohols has been known for some time. This reaction is generally conducted whereby a replacement of the alkoxy group from the alcohol replaces the halide of the halogen silane. The reaction takes place preferably in a solvent in the presence of an acid-binding agent. By means of this general process it is possible to introduce alkoxy groups with the same alkyl radical, with all of the or only a portion of the halogen atoms being exchanged depending on the amount of the alcohol used. In the case of a partial alkoxylation, predominantly mixtures of differing alkoxylation degree are produced. The preparation of partial alkoxylation products of a defined degree of alkoxylation raises particular difficulties if a two-stage process with isolation of the partial alkoxylation product by distillation is not to be employed.

However, when mixed alkoxylation products are prepared, in which the alkyl radicals of the alkoxy groups differ, it is imperative that a pure partial alkoxylation product be obtained for the preparation of pure products. This applies in particular to the preparation of those mixed alkoxylation products that contain, bonded to the silicon atom, one or more tertiary alkoxy radicals in addition to primary or secondary alkoxy radicals. An attempt to produce these products by the aforementioned, generally applicable alkoxylation process results, for the most part, in mixtures of substances consisting of condensates of complicated composition and unusable for the applications of tertiary alkoxy-alkoxysilanes. Thus far, the particular difficulty with respect to the preparation of these mixed alkoxysilanes consisted in producing the preliminary stage of the halogen-containing partial ester at the necessary degree of purity and in producing the same by a simple, uncomplicated method.

It has, therefore, become desirable to provide a simple effective and economic process for the preparation of halogen containing partial esters of silanes. It has become, furthermore, desirable to provide a simple and efficient two-stage process for the preparation of mixed silane esters containing at least one tertiary alkoxy group. Moreover, it has become desirable to provide alkoxysilane partial esters of substantial purity. It has become, furthermore, desirable to provide tertiary alkoxy-alkoxysilane of high purity. Finally it has become desirable to provide a two-step process for the preparation of such tertiary alkoxy-alkoxysilanes in which, as an intermediate, there is prepared halogen-containing partial esters of silicon which need not be separated and purified before undergoing further reaction with a tertiary alcohol en route to the preparation of tertiary alkoxy-alkoxysilanes.

SUMMARY OF THE INVENTION

The long felt desires in this art are answered by a process for the preparation of tertiary alkoxysilanes of the formula

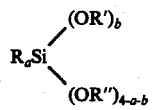

wherein:
R is hydrogen, an alkyl radical of 1 to 4 carbon atoms or an alkenyl radical of $C_2$–$C_{10}$;
R' is alkyl;
R" is tertiary alkyl;
$a$ is 1 or 2;
$b$ is 1 or 2;
$a + b$ does not exceed 3;
by the steps comprising:
a. contacting in the liquid phase and without contacting in the gas phase a halogen-containing silane of the formula $R_aSiX_{4-a}$ where R and $a$ have the previously significance, and X is halogen with a primary or secondary alcohol having the formula R'OH wherein R' has the previously assigned significance, said alcohol is present in an amount not in excess of a 10% stoichiometric excess whereby there is produced a halogen alkoxysilane which is a partial ester; and
b. there after contacting said halogen alkoxysilane with an alcohol of the formula R"OH wherein R" has the previously assigned significance in the presence of an acidbinding agent.

The process can also be carried out employing in step (a) an alcohol of the formula R'OH, wherein R' is a polyhydroxyalkylene group having a terminal hydroxy alkyl group. For instance, the reactant can be a material such as a polyethylene glycol monoether. R' can also be alkylene.

In accordance with the present invention there is obtained a reaction-mixture which contain at least 75%, preferably at least 95% of the desired halogen containing partial ester. The present invention contemplates a process for preparing these halogen-containing partial esters and a continuous process whereby in a single pot reactor the so-formed halogen-containing partial esters are further reacted with a tertiary alcohol in the presence of an acid-binding agent whereby there is synthesized silane esters of tertiary alcohols.

At the heart of the present invention there is the production of high amounts of relatively pure halogen-containing partial esters by reaction of halosilanes with primary and/or secondary alcohols. The process is conducted by introducing the primary and/or secondary alcohols into a reaction vessel containing the silane such that the contact of the silane with the alcohols takes place only in the liquid phase, i.e., the reactants are not contacted in the gaseous phase. The reaction is conducted employing stoichiometric amounts of alcohol and silane. Minor stoichiometric excess quantities of alcohol are tolerated such as an amount up to a 10% stoichiometric excess. Amounts larger than this tend to affect replacement of the remaining halogen atom on the silane ester whereby the ability of the so-formed material to further react with the tertiary alcohol in the second stage is impaired.

The tertiary alkoxy-alkoxysilanes of the present invention are particularly suitable in the preparation of hydrolysis resistent silanes which can be prepared by reacting such tertiary alkoxy-alkoxysilanes with dialkylphosphites. This reaction is generally disclosed in copending application Ser. No. P 23 04 554.7 filed concurrently herewith (Dynamit 780) of Hans Joachim Kötzsch and Hans-Joachim Vahlensieck. Typically, phosphorous organosilane esters of tertiary alcohols are prepared in the manner of that invention by contacting alkenylsilicon esters of the type herein described with dialkylphosphites. The reaction is conducted in the presence of an initiator at a temperature generally between 120° and 150° C. A suitable initiator is a compound of the type disclosed in German federal Pat. No. 1,090,210 and U.S. Pat. No. 3,122,518. A particularly desirable initiator is ditertiary butylperoxide. Generally speaking, the tertiary alkoxy-alkoxysilanes of phosphonic acid esters are prepared by introducing only a portion of the dialkylphosphite reacted into a reaction vessel and then adding to the reaction vessel, the remaining dialkylphosphite to be reacted together with alkenyl tertiary alkoxy-alkoxysilane and initiator. The reaction proceeds by the use of the heat of the reaction generated therein to provide high yields of relatively pure phosphorous organosilane esters of tertiary alcohols which are hydrolysis resistant and are particularly used in the plastics industry. One particular use for these materials is as crosslinking agent for copolymers of ethylenically unsaturated compounds which as the same has a softening effect.

In accordance with the invention numerous different types of tertiary alkoxy-alkoxysilanes can be prepared. It is possible to prepare mixed partial esters of tertiary alcohols wherein each ester group corresponds to a different alkyl group. This is done by employing in the first step a mixture of alcohols such as a primary and secondary alcohol. The amount of these alcohols should be related to the number of halogen atoms to be replaced bearing in mind that on each silane there should remain at least one halogen group for a reaction in a second step with a tertiary alcohol. The second step is performed by reaction with a tertiary alcohol generally tertiary butanol and tertiary pentyl alcohol.

The tertiary alkoxy-alkoxysilanes of the present invention by the process are recovered in excellent yields generally between 75 and 95%. Additionally, they are obtained in a particularly high purity on the order of at least 94% and generally at least 100%.

DESCRIPTION OF PREFERRED EMBODIMENTS

It has, therefore, been found that difficulties inherent in prior art processes can be eliminated if, during the preparation of the preliminary stage of the halogen, e.g., chlorine-containing partial ester, care is taken that while the alcohols are introduced during the first stage reaction, the alcohols do not contact the halogen silane in the gas phase. All of the contact of these materials is in a liquid reaction medium. It has been stated broadly above that the contact of the primary or secondary alcohol with the halogen silane is in the liquid phase. This can be done by two methods. The silane itself can be liquid or it can be dissolved in a suitable solvent such as a halogenated hydrocarbon.

The introduction of the alcohols into the liquid reaction medium can be done by use of an immersion tube. It is not absolutely necessary to introduce exactly a stoichiometric quantity of alcohol as even a slight excess up to about 10% of alcohol can be tolerated. In this case the reaction still proceeds in accordance with the invention. The temperature of the reaction medium in this first process step during the introduction of the alcohol is not particularly critical. It is generally maintained at such a level that the entire system is maintained in a liquid phase. Thus, the partial esterification can be carried out both at room temperature or below the same and even up to the boiling point of the reaction system.

Generally speaking, the reaction is carried out at atmospheric pressure.

During the first reaction stage, mainly the preliminary stage of halogen-containing partial ester is formed corresponding to the stoichiometry of the reactants. The same can be processed immediately thereafter to prepare the tertiary alkoxy-alkoxysilane. However, in a given case the halogen-containing partial ester can be removed. When it is processed immediately thereafter en route to the preparation of tertiary alkoxy-alkoxysilane it is followed by thorough heating to drive off hydrogen halide formed.

The conversion of the preliminary stage of partial ester into the desired tertiary alkoxy-alkoxysilane is done by contacting the partial ester with a tertiary alcohol. This can be done in a manner analagous to the manner of the first stage reaction. The halogen-containing partial ester is reacted with a stoichiometric quantity corresponding to the number of tertiary alkoxy groups to be present on the molecule of a tertiary alcohol in admixture with the stoichiometric quantity of acid acceptor required which quantity depends upon the number of halogen atoms remaining on the silane after the first process step. The acid acceptor is preferably an anhydrous acid acceptor. The hydrogen halide released during the second step reaction is bound by the acid acceptor and can come in a given case, be obtained in the form of a salt.

The reaction product is worked up in a simple manner by applying the usual distillation methods after it has previously been filtered off, filtered off by suction or centrifuged off from the insoluble salt, if desired.

Comparison tests without the use of an immersion tube, in which the alcohol R'OH in the first reaction stage was fed in through the gas phase of the reaction chamber containing hydrogen halide, always resulted in the formation of a non-uniform preliminary stage that was not suitable for the final esterification with the tertiary alcohol by the single-pot method in accordance with the invention, but presented the aforementioned difficulties known from the state of the art.

Due to the production of insoluble by-products, the use of solvents is at times necessary. In these cases it is practical to use solvents that do not dissolve either hydrogen halides or their salts, e.g., chlorinated hydrocarbons such as cis- and trans-dichloroethylene, trichloroethylene, perchloroethylene or liquid hydrocarbons having boiling points of up to 150° C. such as the various gasoline fractions or aromatic hydrocarbons such as, for instance, benzene. If alcoholates are used as acidbinding substances, chlorinated hydrocarbons can of course not be used as solvents.

Suitable starting materials having the general formula $R_aSiX_{4-a}$ are, for instance, trichlorsilane, methyldichlorsilane, ethyldichlorsilane, n-propyldichlorsilane, isobutyldichlorsilane, vinyldichlorsilane, vinyltrichlorsilane, vinylmethyldichlorsilane, dimethyldichlorsilane, propenyltrichlorsilane, allyltrichlorsilane and 3-chloropropyltrichlorsilane and others.

As alcohols having the general formula R'OH for the preparation of the preliminary stage of partial ester having the general formula $R_aSi(OR')_{3-a}X$ there may be used simple aliphatic alcohols especially alkyl alcohols and polymeric polyol such as, for instance, methanol, ethanol, n-propanol, n-butanol, but also, for instance, 2-methoxyethanol or polyethylene-glycolmonoether.

Tertiary alkanols having the general formula R"OH are tertiary pentanol tertiary amyl alcohol and preferably tertiary butanol; as acid acceptors there can be used in particular the tertiary amines such as, for instance, pyridine, the picolines, lutidine, trimethyl amine, triethyl amine, etc. It is, however, also possible to use the aforementioned tertiary alkanols in the form of their alcoholates, e.g., the sodium or potassium tertiary butylate. In this case, the metal component acts as acid acceptor so that the amines can in a given case, be dropped. However, when using hydrogen and chloroalkylsilane compounds as starting materials, alcoholates may not be used.

By the method according to the invention, one can produce silane esters of tertiary alcohols that either have not been obtained in pure form thus far, or have been unknown hitherto. They can be subdivided into hydrogen silane tertiary alkoxy esters having the general formula $HSi(OR')_b(OR'')_{3-b}$, alkyl silane tertiary alkoxy esters having the general formula $R_aSi(OR')_b(OR'')_{4-a-b}$, wherein R represents a $C_1$ to $C_4$ alkyl radical, and alkenyl silane tertiary alkoxy esters, wherein R represents an alkenyl radical and R', R" as well as $a$ and $b$ always have the aforementioned meaning.

Examples for hydrogen silane tertiary alkoxy esters are tertiary butoxydimethoxy silane, tertiary butoxydiethoxy silane, tertiary butoxydi-(2-methoxyethoxy)-silane; as alkylsilane tertiary alkoxy esters there be mentioned, for instance, dimethyl tertiary butoxymethoxy silane, dimethyl tertiary butoxyethoxy silane, dimethyl tertiary butoxy-(2-methoxyethoxy) silane, 3-chloropropyl tertiary butoxydimethoxy silane, 3-chloropropyl tertiary butoxydimethoxy silane, 3-chloropropyl tertiary butoxydiethoxy silane, 3-chloropropyl tertiary butoxydi-(2'-methoxyethoxy)-silane.

Examples for alkylene silane tertiary alkoxy esters which can be produced in accordance with the instant method, are the following compounds: vinyl tertiary butoxymethoxy silane, vinyl tertiary butoxyethoxy silane, vinyl tertiary butoxydimethoxy silane, vinyl tertiary butoxydiethoxy silane, vinylmethyl tertiary butoxymethoxy silane, vinyl tertiary butoxydi-(2-methoxyethoxy)-silane, propenyl tertiary butoxydimethoxy silane, propenyl tertiary butoxydiethoxy silane, allyl tertiary butoxydimethoxy silane, allyl tertiary butoxydiethoxy silane, allyl tertiary butoxy-(2-methoxyethoxy)-silane.

By the method according to the invention, one can also prepare an alkylhydrogen silane tertiary alkoxy esters having the general formula RHSi(OR')(OR") (R, R' and R" have the aforementioned meaning). Compounds that fall within the scope of this general formula are, for instance, methyl tertiary butoxymethoxy silane, methyl tertiary butoxyethoxy silane, ethyl tertiary butoxymethoxy silane, n-propyl tertiary butoxymethoxy silane, isobutyl tertiary butoxymethoxy silane.

The industrial importance of the new compounds that can be made by the process according to the invention is increasing more and more with a view to their use as selective saponification catalysts and as cross-linking agents for the most varied materials on the basis of organic polymers. A number of them, in particular those having the structure R = H, are, furthermore, highly suitable as co-catalysts for the polymerization of olefinic compounds.

In order to more fully illustrate the nature of the invention and the manner of practicing the same, the following examples are presented:

EXAMPLE 1

Preparation of tertiary butoxydimethoxy silane

A solution of 2,710 g of trichlorsilane in 2 liters of trans-dichloroethylene was contained in a 10 liters multi-necked flask equipped with inside thermometer, $N_2$-superposed reflux condenser ($-80°$ C), dropping funnel with an inlet tube opening below the surface of the liquid, blade stirrer, heating and/or cooling coil in the reaction chamber and 25 mm. bottom valve; within approximately 25 minutes, 1,280 g of methanol were introduced via the immersion tube into the solution while stirring. During this operation the temperature dropped to approximately 0° C. Hydrogen chloride developed, which left via the reflux condenser and was collected in milk of lime. After the methanol addition was completed, the residual hydrogen chloride was heated out by boiling under reflux conditions for 5 minutes. Subsequently, while cooling with water at approximately 20° to 40° C and while stirring, a mixture consisting of 1,480 g of tertiary butanol and 1,580 g of pyridine was added within approximately 40 minutes resulting in the precipitation of pyridine hydrochloride. The mixture was stirred for another 20 minutes, filtered off from the precipitate by suction in the cold state (afterwashing with trans-dichloroethylene) and distilled through a packed column containing 60 trays (4 mm. mesh screen rings V4A). After separating the solvent, 1,635 g (80%) of tertiary butoxydimethoxy silane and 192 g of ditertiary butoxymethoxy silane (boiling point (158° C) were obtained in addition to 170 g of trimethoxy silane and 18 g of tetramethoxy silane.

Tertiary butoxydimethoxy silane

Boiling point: 124° to 125° C
$D_4^{20}$: 0.902
$n_D^{20}$: 1.3789
Active hydrogen: 138 Nml/g (calculated 136 Nml/g)

| | Elementary Analysis ($C_6H_{16}O_3Si$, molecular weight 164) | | |
|---|---|---|---|
| | C | H | Si |
| Calculated: | 43.8% | 9.8% | 17.1% |
| Found: | 44.0% | 9.7% | 17.0% |

Ditertiary butoxymethoxy silane

Boiling point: 158° C
$D_4^{20}$: 0.872
$n_D^{20}$: 1.3898

Active hydrogen: 107 Nml/g (calculated 109 Nml/g)

| Elementary Analysis ($C_9H_{22}O_3Si$, molecular weight 206.2) | | | |
|---|---|---|---|
| | C | H | Si |
| Calculated: | 52.3% | 10.7% | 13.7% |
| Found: | 52.5% | 10.8% | 14.0% |

EXAMPLE 2

Preparation of tertiary butoxydiethoxy silane

Analogous to Example 1, 1,840 g of ethanol were added within approximately 25 minutes via the immersion tube to a solution of 2,710 g of trichlorsilane in 2 liters of transdichloroethylene while stirring. In this operation the temperature dropped to approximately 12° C. The further procedure was analogous to Example 1 as well. The working-up by means of a vacuum distillation resulted in a yield of 3,295 g (86%) of tertiary butoxydiethoxy silane.

Boiling point: 46° to 47.5° C (13 Torr)
$D_4^{20}$: 0.864
$n_D^{20}$: 1.3826
Active hydrogen: 118 Nml/g (calculated 116.5 Nml/g)

| Elementary Analysis ($C_8H_{20}O_3Si$, molecular weight 192) | | | |
|---|---|---|---|
| | C | H | Si |
| Calculated: | 49.9% | 10.4% | 14.6% |
| Found: | 50.1% | 10.2% | 14.5% |

EXAMPLE 3

Preparation of tertiary butoxydi-(2-methoxyethoxy)-silane

Analogous to Example 1, 1,520 g of 2-methoxy ethanol were added within approximately 40 minutes via the immersion tube at a temperature of 20° C to a solution of 1,355 g of trichlorsilane in 2 liters of trans]dichloroethylene while stirring. After the hydrogen chloride had been heated out, a mixture consisting of 740 g of tertiary butanol and 790 g of pyridine is added within approximately 30 minutes while cooling with water. The working-up by means of filtering by suction and vacuum distillation resulted in a yield of 2,290 g (91%) of tertiary butoxydi-(2-methoxyethoxy)-silane.

Boiling point: 66° to 68° C (10 Torr)
$D_4^{20}$: 0.989
$n_D^{20}$: 1.4081
Active hydrogen: 90 Nml/g (calculated 89 Nml/g)

| Elementary Analysis ($C_{10}H_{24}O_5Si$, molecular weight 252) | | | |
|---|---|---|---|
| | C | H | Si |
| Calculated: | 47.6% | 9.5% | 11.1% |
| Found: | 47.8% | 9.5% | 10.8% |

EXAMPLE 4

Preparation of vinyl tertiary butoxydiethoxy silane

Analogous to Example 1, 920 g of ethanol were added within 25 minutes via the immersion tube to a solution of 1,615 g of vinyltrichlorsilane in 3 liters of trichloroethylene, and subsequently the residual hydrogen chloride was heated out. Thereupon, a mixture consisting of 740 g of tertiary butanol and 790 g of pyridine was added at approximately 80° C, and stirring was continued for 1 hour at 90° C. Working-up by means of filtering off by suction and vacuum distillation resulted in a yield of 1,825 g (84%) of vinyl tertiary butoxydiethoxy silane in addition to 180 g of vinyltriethoxy silane.

Boiling point: 78° to 79° (10 Torr)
$D_4^{20}$: 0.889
$n_D^{20}$: 1.4001

| Elementary Analysis ($C_{10}H_{22}O_3Si$, molecular weight 218) | | | |
|---|---|---|---|
| | C | H | Si |
| Calculated: | 55.0% | 10.1% | 12.8% |
| Found: | 55.2% | 9.9% | 12.7% |

Generally speaking, acid-binding agent is employed in at least a stoichiometric amount relevant to the number of halogen atoms remaining on the partial silane ester to be exchanged during the reaction with the tertiary alcohol. Preferably, the acid-binding agent is present in such stoichiometric amount up to a stoichiometric excess of about 1 – 2%.

What is claimed is:

1. An alkoxysilane of the formula

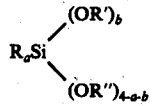

wherein R is hydrogen, or an alkenyl radical of $C_2$–$C_{10}$;
R' is alkyl of 1–8 carbon atoms, alkylene or a polyhydroxy alkylene group having a terminal hydroxy alkyl group;
R" is a tertiary alkyl of 4 to 8 carbon atoms;
a is 1 or 2;
b is 1 or 2; and
a + b does not exceed 3.

2. An alkoxysilane according to claim 1 wherein R is hydrogen.

3. An alkoxysilane according to claim 2 wherein R' is an alkyl radical of 1 to 4 carbon atoms.

4. An alkoxysilane according to claim 3 wherein R" is a tertiary alkyl of 4–5 carbon atoms.

5. An alkoxysilane according to claim 4 wherein b equals 1.

6. An alkoxysilane according to claim 4 wherein b equals 2.

7. An alkoxysilane according to claim 1 wherein R equals alkenyl of $C_2$–$C_{10}$.

8. An alkoxysilane according to claim 7 wherein R is an alkenyl group of $C_2$–$C_3$.

9. An alkoxysilane according to claim 8 wherein R' is an alkyl group of 1 to 4 carbon atoms.

10. An alkoxysilane according to claim 7 wherein b equals 1.

11. An alkoxysilane according to claim 10 wherein b equals 2.

12. An alkoxysilane according to claim 1 which is a tertiary butoxydimethoxy silane having the formula

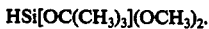

13. An alkoxysilane according to claim 1 which silane is a ditertiarybutoxymethoxy silane having the formula

14. An alkoxysilane according to claim 1 which is a tertiary butoxydi-(2-methoxyethoxy)-silane having the formula HSi[OC(CH$_3$)$_3$](OC$_2$H$_4$OCH$_3$)$_2$.

15. An alkoxysilane according to claim 1 which is a vinyltertiary butoxydiethoxysilane having the formula CH$_2$=CHSi[OC(CH$_3$)$_3$](OC$_2$H$_5$)$_2$.

16. An alkoxysilane according to claim 1 wherein $b$ equal 1.

17. A process for preparing a compound of claim 1 which comprises the steps of:
A. contacting in the liquid phase and without contacting in the gas phase hydrogen silane of the formula R$_a$SiX$_{4-a}$ wherein R is hydrogen, alkenyl of C$_2$-C$_{10}$ or alkyl of C$_1$-C$_4$, $a$ is 1 or 2 and X is halogen, with a primary or secondary alcohol having the formula R'OH wherein R' is an alkyl group, an alkylene group or a polyhydroxyalkylene group having a terminal hydroxy alkyl group; said alcohol present in an amount not in excess of a 10% stoichiometric excess relative to the halogen alkoxysilane thereby produced;
B. thereafter without isolating the resultant halogen alkoxysilane from step A contacting said halogen alkoxysilane with an alcohol of the formula R''OH wherein R'' is a tertiary alkyl group of C$_4$-C$_8$ in the presence of an acid binding agent.

18. A process according to claim 17 wherein said acid-binding acceptor is selected from the group consisting of pyridene, apicoline, lutidine, trimethylamine and triethylamine.

19. A process according to claim 17 wherein step A is conducted by initially charging a reaction vessel with the halogen silane and introducing into such halogen silane through an immersion tube said primary or secondary alcohol.

20. A process according to claim 19 wherein the halogen silane is dissolved in a solvent in the reaction vessel.

21. A process according to claim 20 wherein the solvent is a chlorinated hydrocarbon.

22. A process according to claim 21 wherein the chlorinated hydrocarbon is selected from the group consisting of cis-dichloroethylene, trans-dichloroethylene, trichloroethylene, and perchloroethylene.

23. A process according to claim 20 wherein the halogen silane is selected from the group consisting of trichlorsilane, methyldichlorsilane, ethyldichlorsilane, n-propyldichlorsilane, isobutyldichlorsilane, vinyldichlorsilane, vinyltrichlorsilane, vinylmethyldichlorsilane, dimethyldichlorsilane, propenyltrichlorsilane, allyltrichlorsilane and 3-chloropropyltrichlorsilane.

24. A process according to claim 23 wherein the alcohol of the formula R'OH is selected from the group consisting of methanol, ethanol, normal propanol, normal butanol, 2-methoxyethanol and polyethylene glycol monoether.

25. A process according to claim 24 wherein the tertiary alcohol is selected from the group consisting of tertiary butanol, tertiary pentyl alcohol and tertiary amyl alcohol.

26. A composition of claim 1 which is present in a purity of at least 94%.

27. A composition of claim 1 which is 100% pure.

28. A process according to claim 17 wherein to the reaction mixture of step A there is introduced, following formation of the intermediate halogen alkoxysilane and without any purification or isolation thereof, said alcohol of the formula R'OH.

29. A process according to claim 28 wherein R is hydrogen.

30. A process according to claim 28 wherein R is alkenyl of C$_2$-C$_{10}$.

31. An alkoxysilane of the formula

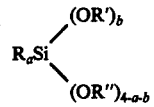

wherein R is hydrogen, an alkyl radical of 1 to 4 carbon atoms or an alkenyl radical of C$_2$-C$_{10}$, R' is alkyl of 1 to 8 carbon atoms and R'' is tertiary alkyl of 4 to 8 carbon atoms, $a$ is 1 or 2, $b$ is 1 or 2 and $a$ plus $b$ does not exceed 3, which is at least 94% pure, produced by a process comprising the steps of:
A. contacting in the liquid phase and without contacting in the gas phase halogen silane of the formula R$_a$SiX$_{4-a}$ wherein R is hydrogen, alkenyl of C$_2$-C$_{10}$ or alkyl of C$_1$-C$_4$, $a$ is 1 or 2 and X is halogen, with a primary or secondary alcohol having the formula R'OH wherein R' is an alkyl group, an alkylene group or a polyhydroxyalkylene group having a terminal hydroxy alkyl group; said alcohol present in an amount not in excess of a 10% stoichiometric excess whereby to produce a halogen alkoxysilane as an intermediate;
B. thereafter contacting said halogen alkoxysilane while in the reaction mixture of step A with an alcohol of the formula R'OH wherein R' is a tertiary alkyl group of C$_4$-C$_8$ in the presence of an acid binding agent.

32. An alkoxysilane of the formula

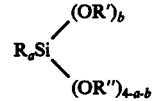

wherein
R is hydrogen, an alkyl radical of 1 to 4 carbon atoms or an alkenyl radical of C$_2$-C$_{10}$;
R' is alkyl of 1 to 8 carbon atoms, alkylene or a polyhydroxyl alkylene group having a terminal hydroxy alkyl group;
R'' is a tertiary alkyl of 4 to 8 carbon atoms;
$a$ is 1; and
$b$ is 1.

* * * * *

UNITED STATES PATENT AND TRADEMARK OFFICE
CERTIFICATE OF CORRECTION

PATENT NO. : 4,060,538
DATED : November 29, 1977
INVENTOR(S) : Hans Joachim Kötzsch et al It is certified that error appears in the above-identified patent and that said Letters Patent are hereby corrected as shown below:

Column 7, line 55, "$C_{10}H-O_5Si$" should read -- $C_{10}H_{24}O_5Si$ --.

Signed and Sealed this

Thirtieth Day of May 1978

[SEAL]

Attest:

RUTH C. MASON
Attesting Officer

LUTRELLE F. PARKER
Acting Commissioner of Patents and Trademarks